United States Patent [19]

Sunnanväder et al.

[11] Patent Number: 4,960,259
[45] Date of Patent: Oct. 2, 1990

[54] SHUT-OFF VALVE FOR A LIQUID FLOW LINE OR INFUSION DEVICE

[75] Inventors: Lars Sunnanväder, Hechingen; Tomas Hartig, Hechingen-Bechtoldsweiler, both of Fed. Rep. of Germany

[73] Assignee: Joka Kathetertechnik GmbH, Fed. Rep. of Germany

[21] Appl. No.: 329,733

[22] Filed: Mar. 28, 1989

[51] Int. Cl.⁵ .............................................. F16K 7/04
[52] U.S. Cl. ........................................ 251/7; 604/250
[58] Field of Search ..................... 251/4, 7; 604/250

[56] References Cited

U.S. PATENT DOCUMENTS

| | | | |
|---|---|---|---|
| 4,146,018 | 3/1979 | Aldridge et al. | 251/7 |
| 4,440,378 | 4/1984 | Sullivan | 251/4 X |
| 4,624,663 | 11/1986 | Danby et al. | 251/7 X |

FOREIGN PATENT DOCUMENTS

| | | | |
|---|---|---|---|
| 325162 | 3/1935 | Italy | 251/8 |
| 378623 | 6/1964 | Switzerland | 251/8 |
| 1242222 | 8/1971 | United Kingdom | 251/8 |

Primary Examiner—John C. Fox
Attorney, Agent, or Firm—Biebel, French & Nauman

[57] ABSTRACT

A shut-off valve for a fluid flow or an infusion instrument is described. A sleeve-form casing (2) with a lateral opening (4) between its ends is provided. An elastic tube piece (7) lies within casing (2) to allow fluid flow therethrough. A pressure body (14) is movable radially within the lateral opening (4) to selectively compress or not compress the tube piece (7) so as to occlude or open fluid flow through the tube piece (7). For simplification of manufacture and for quick operation of such a shut-off valve, especially without painful or injurious activities in operation, a tubular guide sleeve (8) is provided and surrounds the lateral opening (4) of the casing. Sleeve (8) is arranged to laterally project from the casing (2) and includes at least one pair of blocking stops (10, 10', 11 11'). The pressure body (14) has a plug shape. On the end of the pressure body (14), facing away from the tube piece (7), there is fastened a cap (16) with an elastic mantle (12) and snap ring (18) depending from the cap. The snap ring at least partially overlaps the guide sleeve (8).

5 Claims, 4 Drawing Sheets

SHUT-OFF VALVE FOR A LIQUID FLOW LINE OR INFUSION DEVICE

FIELD OF THE INVENTION

The invention relates to a shut-off valve assembly for a liquid flow line or infusion device having a sleeve-like casing with a lateral opening between its ends. In the zone of the lateral opening there is installed an elastic flexible tube piece lying with sealing effect along the inner wall of the casing, proximate the opening. A pressure body is radially movable in the lateral opening with respect to the axis of the casing to selectively close or open fluid flow-through the line by selectively compressing or not compressing the flexible tube piece.

BACKGROUND OF THE INVENTION

Shut-off devices for infusion devices or blood-drawing devices are already known that can be connected by flexible tubes or injection syringes to an emplaced catheter in order to supply an infusion fluid to a patient or in order to remove blood or other body fluids from the patient.

In order to shut-off fluid flow of such a connection both after completion of the catheterizing process and also in the case of an emplaced catheter, a cannula closure piece with a sleeve-like casing of the type described above has been utilized. In such devices a pressure body is constructed as a pair of balls, each of which is arranged along a diametrically opposite lateral side of the flow passage and its associated elastic tube piece. A U-shaped pusher grips both balls and in one of its end positions permits the tube piece to leave the passage free and open, while in the other end position of the pusher, the balls are moved toward one another to close the passage.

This known cannula connection, however, is not only complicated in construction, but, above all, the movement direction or stroke of the pusher or actuator extends lengthwise in the direction of the cannula, whereby the operator must use two hands in order to use the device. Furthermore, the movement of the pusher or actuator in the direction of the operating cannula frequently causes (blood) vessel injuries; and as can be vividly imagined, catheterizing with such an instrument can be extremely painful.

Accordingly, there is a need in the art for the provision of a shut-off valve or device of the type mentioned that is not only simple to produce and easy to operate, but is capable of being operated without resulting in injury or severe pain to the patient.

SUMMARY OF THE INVENTION

This and other problems in the art are solved according to the invention by the provision of a tubular guide sleeve which surrounds and protects the lateral opening of the casing. At least one pair of blocking stops is provided on the guide sleeve. A pressure body in the form of a plug is slidably received in the guide sleeve. A cap is fastened to one end of the pressure body and carries an elastic mantle and a snap ring that, at least partially overlap the guide sleeve.

By the use of such structures, the operating movement direction or motion of the shut-off valve is adjusted so as to be transversely oriented with respect to the longitudinal direction of the associated cannula so that several advantages are provided. Actuation of the valve by the physician or the nurse no longer causes painful effects and injuries to blood vessels. Additionally, thumb movement can be better coordinated in the radial direction with respect to the axis of the sleeve-like casing. Furthermore, operating personnel can execute the valve operation with only one hand, so that the other hand remains free for other activities. Thereby the danger of infection of the operating personnel during the treatment of the patient is reduced.

Application of pressure on the plug-shaped pressure body compresses the tube piece in the direction transverse to the longitudinal axis of the tube piece so that the passage channel is either choked or completely closed to effect a seal. The snap ring grips on the mantle slide over the blocking stops and make possible, without further actuation, of an arrest of the pressure body in a predetermined position, without the necessity of providing any complicated parts. The cap on the upper, distal, end of the pressure plug has the form of a disk, whose plane lies transversely to the longitudinal direction of the pressure plug. On the circumference of this disk, elastic mantle members are arranged and extend in the longitudinal direction of pressure plug spaced from the longitudinal axis of the pressure plug. This elastic mantle is open along the side facing the sleeve-shaped casing. At this lower end of the mantle, a narrow collar or snap ring is provided.

The inside diameter of the snap ring is such that it can be deflected transversely with respect to the longitudinal axis of the pressure plug and thus engage the blocking stop members provided on the guide sleeve. A pair of blocking stop members cooperate with the mantle, the cap and the pressure body to ensure central, symmetrical disposition of the pressure plug within the guide sleeve so that the pressure plug is not tilted during usage. If, for example, the snap ring, during its downward sliding motion, overruns one or both of the blocking stops, the mantle may be compressed between two fingers, whereby it is ovalized in plan view. If then the blocking stops are present in the zone of the major axis of this oval, then it is possible directly to lift or slide the snap ring up over the blocking stops in order, for example, to push the pressure plug again radially outwardly from the tube piece to open the passage for the flow of medicament, body fluid or other desired fluid therethrough.

In accordance with the invention, the passage channel for the body fluids in the sleeve-shaped casing may be only partially or completely closed. For example, in certain applications, a steel cannula is thrust through the tube piece and into a catheter tube in the casing. Upon actuation of the pressure body by pressing on the cap with the thumb, the proximal or front end of the pressure plug is pressed against the tube piece in such a way that the tube piece lays itself around the steel cannula. This intermediate state can be achieved, for example, by lightly pressing on the pressure body. In the meantime, then, the steel cannula can be extracted without allowing body fluid to escape past the tube piece to the outside. During the application of this light pressure on the pressure body, the steel cannula or needle may be withdrawn. The elastic tube piece fits itself around the surface of the steel cannula or needle and seals this off so that, for example, no blood can spray out between the needle and the tube piece. After complete withdrawal of the needle or cannula, the tube piece then seals off the entire passage completely if the light pressure on the pressure body is increased.

It is obvious that such a shut-off value can also be used as a closure valve for injection devices.

In another advantageous embodiment of the invention, the snap ring has a truncated-conical surface expanding in the direction of the casing. It is preferred that the plug-shaped pressure body itself be solid or rigid in order to effectively transfer the pressure needed for the compression of the tube piece from the thumb to the tube piece. On the other hand, it is preferred to provide an elastic mantle so that this member can be manually compressed in order to simplify production and operation of the device. The snap ring should also be elastically bendable and compressible and can advantageously be made of the same plastic as the mantle. The provision of a tapered converging oblique surface in the zone of the snap ring combined with the softness of the material assures an easy shifting or sliding motion of the snap ring over the blocking stop or stops.

Another advantage of the invention is the arrangement of the blocking stops. Preferably, each blocking stop of a pair is arranged on the outer circumference of the guide sleeve, lying diametrically opposite (180° away from) the other member of the pair, and at the same height spacing as the other member of the pair as measured radially outwardly from the casing. Through the diametrically opposite disposition of the two blocking stops of the pair, the proper guidance of the pressure plug properly into the guide sleeve is facilitated. As viewed in plan view in the direction of the axis of the guide sleeve, each blocking stop projects radially outwardly, i.e., laterally to the longitudinal direction of the guide sleeve, like an annular part. Preferably, each annular part is just as long as the annular part diametrically opposite thereto and is provided in radial direction with an expansion such that the outer edge of each of the annular blocking stops lies virtually snug with the elastic mantle. It is preferred to provide the elastic mantle with diametrically disposed openings or slits, through which the block stops can protrude. In this manner, the elastic mantle and the pressure body are simultaneously properly guided into the guide sleeve by the blocking stops.

It is advantageous to provide two pairs of blocking stops wherein each pair is angularly spaced and disposed at a different height as measured along the longitudinal axis of the guide sleeve from the other pair. Each blocking stop extends perpendicularly to the longitudinal direction of the guide sleeve. According to the invention, therefore, there is provided a lower pair of blocking stops seated more closely to the casing than the upper or outer pair of blocking stops. Both pairs are arranged at different heights as measured along the longitudinal axis of the guide sleeve and, furthermore, each pair is angularly offset with respect to the other pair. If one views the guide sleeve in an axial direction from the top, then the connecting line of a pair of blocking stops lies, for example, at a right angle to the connecting line of the second pair of blocking stops. If the angular spacing of the respective blocking stops, as seen in axial direction of the guide sleeve, is small enough, for example within an angle of about 45°, then suitably large-dimensions breaks openings or slits in the elastic mantle can be provided to accommodate both pairs of block stops. The mantle is then arranged in four columns, each column being spaced from each other around the circumference of an annulus, but, as before, the mantle still fulfills the function of an elastic mantle, i.e., it is compressible if one presses on these columns from outside, and is therefore capable of forming an oval shape upon such compression to allow it to lift over the lower blocking stops so as to disengage the pressure part from the arrest or stop position.

Another advantage of the invention is achieved if the height spacing of the two pairs of block stops from one another is greater than the deformation path of the tube piece. In such manner, the user of the device knows that the tube piece is not only partially but completely compressed when the pressure body has run through its full stroke as measured from the uppermost pair of stops to the lower pair.

The lower pair of blocking stops is provided with a truncated-conical surface in such a way that the frustum of the cone tapers in the direction toward the snap ring. This meets the sliding movement of the snap ring. In this manner, the user can slide the snap ring easily over the lower pair of blocking stops. Conversely, this arrest position (for example complete closing of the tube piece) can be reversed by compressing the mantle into an oval cross-sectioned shape and then by lifting the ovalized mantle over the lower pair of block stops.

The outer periphery of the upper pair of blocking stops, which is angularly offset by 90° from the lower inner blocking stops, is not provided with a beveled surface. Here, the upper blocking stops function to prevent lifting-off or pulling out of the pressure body from the shut-off device.

In another embodiment of the invention, a thread is provided on the inner surface of the elastic mantle to engage with at least one bulge or outside thread provided on the outside of the guide sleeve. This structure has the advantage that the passage for the body fluid in the tube piece cannot inadvertently be squeezed off by an inadvertent jolt or application of pressure from above on the pressure body. A deliberate turning or disengagement of the engaging mantle and guide sleeve members is required in order to actuate closing of the tube piece. The screw movement permits an especially careful and precise adjustment of the pressure body in order to actuate complete closing of the passage in the tube piece.

In all forms of the invention, the pressure body is accurately guided in its sliding motion within the guide sleeve and tilting of the pressure body is also minimized during operation. Preferably, this accurate sliding contact is provided both on the upper and also lower end of the guide sleeve.

The inside diameter of the guide sleeve is greater than the outside diameter of the lateral opening in the casing, and the tapered free end (i.e., proximal end) of the pressure body facing the tube piece. The guide sleeve and its associated blocking stops should be larger in diameter than the outside diameter of the tube piece. The free, inner or lower end of the pressure plug, on the other hand, should not be too large in relation to the outside diameter of the tube piece. In the compression stroke of the pressure body, the tapered end of the pressure body should have about the same dimension as the flow passage provided in the tube piece. By the provision of a tapered pressure body, there is achieved a good distribution of weight and less shifting-around of the tube material during the compression of the tube piece. Less force is required for the compression of the tube piece and the tube piece does not tend to deflect to the side of the tapered pressure body under the strain of compression.

Other advantages, features and applications of the present invention are apparent from the following description of preferred embodiments of the invention taken in conjunction with the appended drawings.

DETAILED DESCRIPTION OF THE PREFERRED EMBODIMENT

Figure 1:
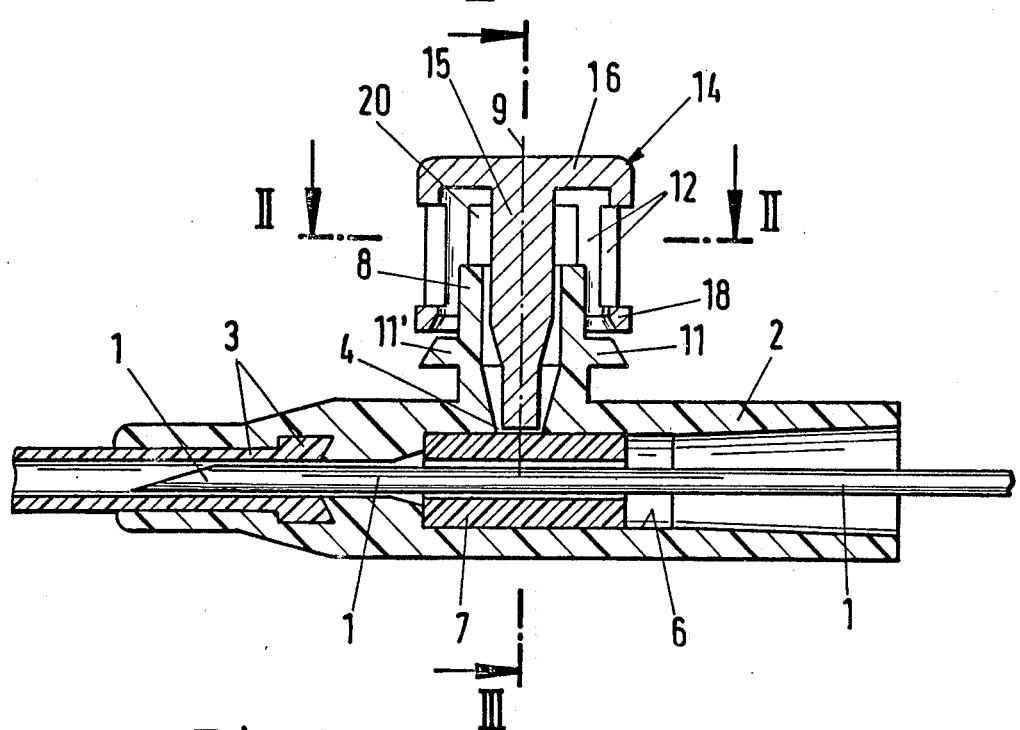
FIG. 1 is a cutaway, longitudinal section view of a shut-off valve in accordance with the invention showing the open position of the fluid passage.

The shut-off valve is shown here in conjunction with an infusion cannula, the steel cannula 1 being show thrust partially into the tubular casing 2. From the rear or operating side (to the right in FIGS. 1 and 5) the casing 2 is provided with a connecting sleeve (not designated in detail) which on the inside is slightly conical and serves for the connection to an injection syringe, a tube line or the like. On the opposite or front side of the casing 1 there is seen the inserted catheter tube 3, into which the steel cannula 1 is thrust.

The casing 2 in the representation above is provided with a lateral opening 4 between its ends. Under this opening 4 and in the zone of the same, namely in longitudinal direction 5 (FIG. 2) of the casing 2 to the front and to the rear, there is installed, lying on the inner wall 6, a tube piece 7, which is made of elastic material, for example, silicone. This tube piece 7 is easily flexible and seals off against the inner wall 6 of the casing 2. This sealing occurs in the representation of FIG. 1, except for the surface of the opening 4, in the entire area of the outer surface of the tube piece 7. In contrast, in FIG. 5, a seal is provided only at the ends of the tube piece, because tube piece 7 is compressed in the middle. It can be seen that in the open passage state (FIG. 1), the steel cannula 1 is led through the tube piece 7 into catheter tube 3.

Surrounding the lateral opening 4 of the casing 2 a tubular guide sleeve 8 is provided and may be molded integrally with casing 2. The preferred plastic material for guide sleeve 8 and casing 2 is polyethylene. The longitudinal axis 9 of the guide sleeve 8 lies, as can be seen, perpendicular to the longitudinal axis 5 of the casing 2. For this reason, the guide sleeve 8 is regarded as projecting radially outwardly from the side of the casing 2.

Figure 2:
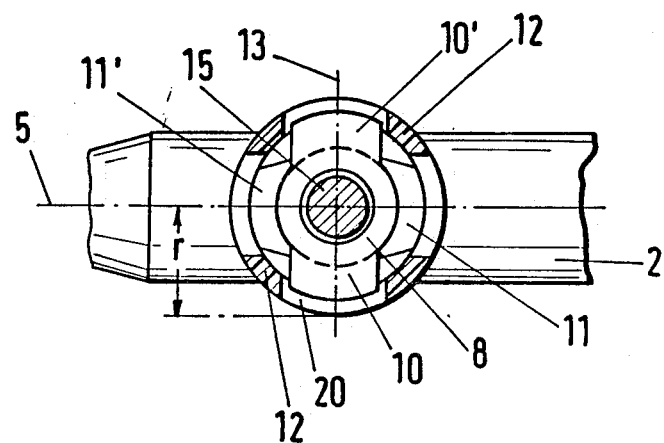
FIG. 2 is a sectional view taken along the lines and arrows II—II of FIG. 1.

Two pairs of blocking stops, 10, 10', 11, 11' are molded in annular-part form projecting radially outward from the guide sleeve 8 (FIG. 2). In each pair, each of the blocking stops, 10, 10', 11, 11' forming a pair stand diametrically opposite the other in the pair. They are connected to the outer circumference of the guide sleeve 8 and end at a distance from the central axis 9 of the guide sleeve 8, which is somewhat smaller than the radius of the mantle 12 still to be described later. There is present a lower pair of blocking stops 11, 11', which lie nearer the casing 2 than the upper or outer pair of blocking stops 10, 10', which outer or upper blocking stops are arranged at a height spacing "a" (FIG. 5) from the lower or inner pair of blocking stops 11, 11'. From FIGS. 2 and 6, (i.e., from a direction looking downwardly in the axial direction 9 of the guide sleeve 8), it is perceived that the connecting line of the two blocking stops 11, 11' which coincides with the longitudinal direction 5, runs perpendicular to the connecting line 13 of the blocking stops 10, 10'. The two pairs of blocking stops, therefore, are arranged at an angular spacing of 90° relative to each other.

Figure 3:
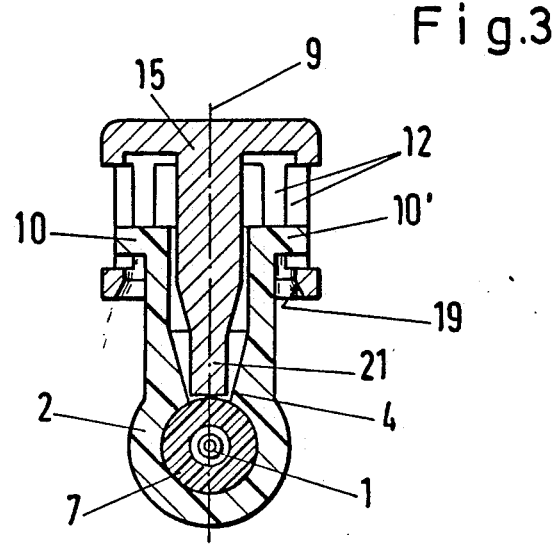
FIG. 3 is a sectional view taken along the lines and arrows III—III of FIG. 1.

While the upper pair of blocking stops 10, 10', (which are clearly shown in FIGS. 3 and 4) have a straight cross-sectional profile, the outer radial surface of the lower blocking stops 11, 11', (as can be seen best from FIGS. 1 and 5) presents a truncated-conically tapered cross-section in such a way that the truncated cone apex lies perpendicular to the axial line 9 outside the guide sleeve 8. The frustum presents a beveled outer surface that slopes outwardly from top to bottom.

The pressure body, designated generally as 14, consists essentially of the plug-shaped part 15, which has on its outer distal, upper end an annular cap 16, and an elastic mantle 12, depending from the cap 16. Molded onto the lower, inner end of mantle 12 is the snap ring 18. Snap ring 18 has a truncated conical surface 19 expanding in the direction of the casing 2, which mates with the above-described truncated-conical surface of the blocking stops 11, 11'.

Because the radial length of the blocking stops is only slightly smaller than the radius r of the outside diameter of the mantle 12 (FIGS. 2 and 4), there are formed elongated openings or slits 20 in the elastic mantle 12, between which openings or slits, the mantle 12 remains standing in the manner of columns.

The cross-sectional pressure plug 15 and surrounding guide sleeve 8 have in their upper zones diameters that are greater than the lower nozzle zone proximate the tube piece 7. This means that the pressure plug 15 in its lower inner third is constructed as a tapered plug 21. The actual pressure surface, therefore, is about as large as the surface of the lateral opening 4 in the casing 2.

Figure 7:
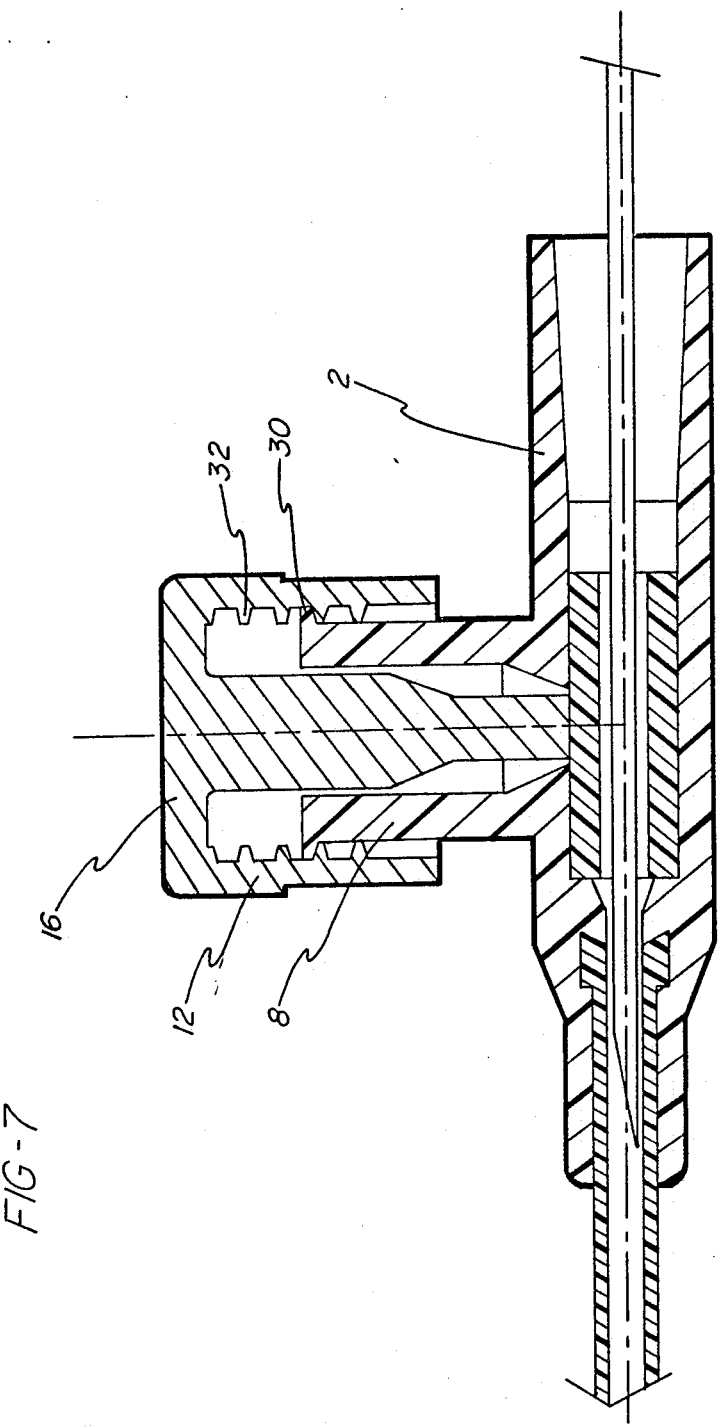
FIG. 7 is a view similar to FIG. 1 of another embodiment of the invention.

Turning now to the embodiment shown in FIG. 7, a plurality of threads 32 are arranged on the inside annular surface of mantle 12. Threads 32 mate with threads 30 formed on the outside of guide sleeve 8. This particular embodiment provides advantage in that the passage for body fluid within the tube piece cannot be inadvertently squeezed off by a pressure or jolt from above on the pressure body. For the choking or complete squeezing off and closing of the tube piece, a deliberate turning motion is required. The screw movement permits an especially careful and precise adjustment of the pressure body and the attendant choking of the passage in the tube piece.

In operation, as the steel cannula 1 is withdrawn, the operator begins to close the fluid passage by the application of pressure on body 14. In other words, the pressure plug 15 moves inwardly and downwardly in the direction of the tube piece 7 and squeezes this partly together under light pressure, while the steel cannula 1 is still being withdrawn.

Figure 4:
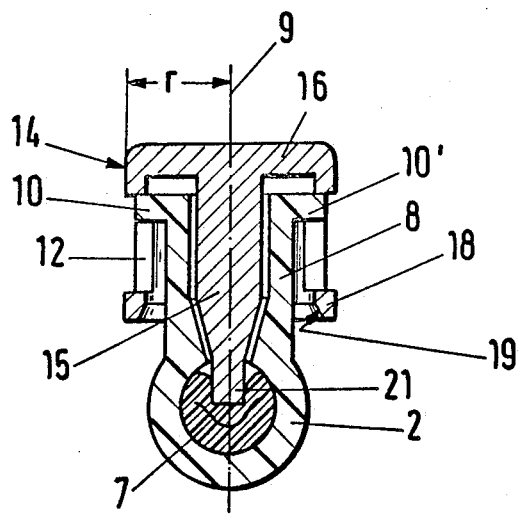
FIG. 4 is a sectional view similar to FIG. 3, but taken along the lines and arrows IV—IV of FIG. 5, showing the tube piece completely compressed to stop fluid flow therethrough.
Figure 5:
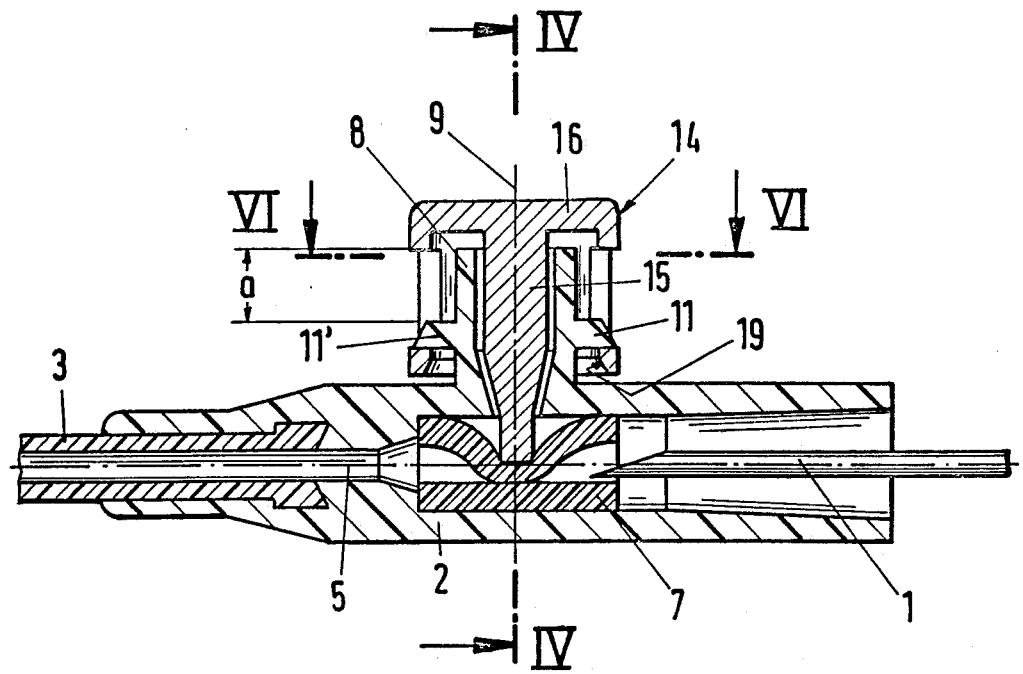
FIG. 5 is a cutaway, longitudinal section similar to FIG. 1, but with the pressure body thrust completely downward showing full compression of the tube piece to stop fluid flow therethrough.
Figure 6:
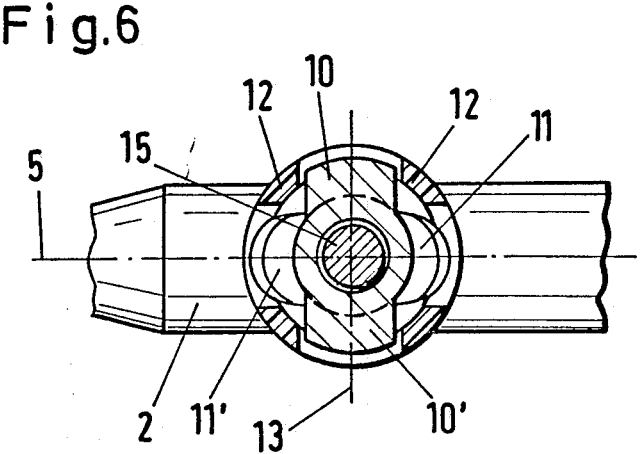
FIG. 6 is a sectional view taken along the lines and arrows VI—VI of FIG. 5.

Then, the plug 15 continues its inward, downward stroke until it reaches the state shown in FIGS. 4 to 6. Here, the complete compression of the tapered plug 21 into the tube piece 7 is made in the passage, just as the tapered point of the steel cannula 1 is drawn out of the tube piece 7. The tapered pressure plug 21 (FIG. 4) is in its end position. According to FIG. 4, the silicone material of the tube piece 7 is evenly distributed about the outer surfaces of the plug part 21. The passage proper in the tube piece 7 has been compressed as shown in FIG. 4 into a U-shaped line. The sealing is complete, the shut-off valve has reached its sealing end position and fluid flow through the passage is occluded.

In this position the snap ring 18 has been slid over the lower inner blocking stops 11, 11' and has snapped in place underneath these (FIG. 5). Thereby a stop position has been reached which can be disengaged only if, according to representation of FIG. 6, compressive pressure is applied from above and below, and the mantle 12, therefore, is compressed into an oval plan shape in such a way that its major axis lies in the direction of the longitudinal axis 5 of the cannula. Only then can the snap ring parts be drawn up again over the blocking stops 11, 11'. The elastic recovery force of the tube piece 7 contributes to the upward raising of the snap ring parts over the blocking stops 11, 11'.

During the upward stroke or movement of plug 15, a slipping over of the snap ring over the upper blocking stops 10, 10' is not desired. It is seen from FIG. 3 that stops 10, 10' abut the top portion of surface 19 of the snap ring to limit upward movement of plug 15. If the snap ring 18 were allowed to slide over the outer blocking stops 10, 10', then the pressure body 14 could be separated from the whole shut-off device. Such separation is undesirable for normal operation and is to be avoided.

The opening and closing of the fluid passage can be repeated at any time during the treatment.

It is to be understood that the principles of the invention are not to be limited to the specific embodiments illustrated and described above and that the invention is intended to include modifications and variations of the above that may be made without departing from the spirit of the present invention and the scope of the appended claims.

We claim:

1. In a shut-off valve apparatus for a fluid flow device of the type having a sleeve-form casing (2) with a lateral opening (4) disposed between end-wise portions of the casing, an elastic flexible tube piece (7) lying within the casing (2) adapted to permit fluid flow therethrough, and a pressure body means (14) movable radially within the lateral opening (4) for selectively compressing the flexible tube piece (7) to stop fluid flow through the flexible tube piece (7), the improvement comprising, in combination, a guide sleeve (8) surrounding the lateral opening (4) and extending radially outwardly from the casing (2), the guide sleeve comprising at least one pair of blocking stop members (10, 10', 11, 11'), the pressure body carrying an elastic mantle (12) having a snap ring (18) depending therefrom, said snap ring (18) being engageable with at least one pair of the blocking stop members during the compression, the pressure body (14) comprising a cap (16) from which the mantle and snap ring (18) depend, the pressure body (14), cap (16), mantle (12) and snap ring (18) comprising an integral plastic structure, two pairs of blocking stops (10, 10', 11, 11') being provided which depend radially outwardly from the outside of the guide sleeve (8), each stop in a pair lying diametrically opposite from the other stop in the pair and each stop in a pair lying at the same axial distance from the casing (2) along the sleeve (8) as the other stop in the pair, wherein each pair of the blocking stops is disposed at a different height than the other pair along the sleeve (8) in the axial dimension of the sleeve (8) and wherein each pair is angularly offset with respect to the other pair in the radial direction of the sleeve (8).

2. Apparatus as recited in claim 1 wherein the difference in height of the paris of stops is greater than the zone of compression of the tube piece (7).

3. Apparatus as recited in claim 2 wherein the pressure body means (14) is slidably disposed within the guide sleeve (8).

4. Apparatus as recited in claim 3 wherein the inside diameter of guide sleeve (8) is greater than the diameter of lateral opening (4) and the pressure body means (14) comprises a tapered portion adapted to compress the tube piece (7).

5. Apparatus as recited in claim 5 wherein said snap ring comprises a bevelled outer surface (19) that slopes radially outwardly from top to bottom.

* * * * *

UNITED STATES PATENT AND TRADEMARK OFFICE
CERTIFICATE OF CORRECTION

PATENT NO. : 4,960,259

DATED : October 2, 1990

INVENTOR(S) : Lars Sunnanvader and Tomas Hartig

It is certified that error appears in the above-identified patent and that said Letters Patent is hereby corrected as shown below:

Column 8, claim 5, line 44, "claim 5" should be --claim 1--.

Signed and Sealed this

Tenth Day of March, 1992

Attest:

HARRY F. MANBECK, JR.

*Attesting Officer*  *Commissioner of Patents and Trademarks*